United States Patent [19]

Jon et al.

[11] 4,232,558

[45] Nov. 11, 1980

[54] METHODS FOR DETERMINING BOND FAILURE MODES USING STRESS WAVE EMISSION TECHNIQUES

[75] Inventors: Min-Chung Jon; Vito Palazzo, both of East Windsor Township, Mercer County, N.J.

[73] Assignee: Western Electric Company, Inc., New York, N.Y.

[21] Appl. No.: 29,174

[22] Filed: Apr. 12, 1979

[51] Int. Cl.³ ............................................. G01N 29/00
[52] U.S. Cl. ..................................................... 73/801
[58] Field of Search ..................... 73/801, 827, 150 A, 73/587

[56] References Cited

U.S. PATENT DOCUMENTS

| | | | |
|---|---|---|---|
| 3,924,456 | 12/1975 | Vahaviolos | 73/801 |
| 3,969,927 | 7/1976 | Yoshida et al. | 73/587 |
| 4,004,456 | 1/1977 | Vahaviolos | 73/801 |
| 4,090,400 | 5/1978 | Vahaviolos | 73/801 |

OTHER PUBLICATIONS

G. G. Harman, "The Use of Acoustic Emission in a Test for Beam Lead Bond Integrity", NBS, 14th Annual Proceedings IEEE Reliability Physics, Apr. 20-22, 1976.

*Primary Examiner*—Anthony V. Ciarlante
*Attorney, Agent, or Firm*—D. J. Kirk

[57] ABSTRACT

As leads that have been thermocompressively bonded to ceramic substrates are pulled to destruction, stress waves are monitored and counted. The total count is compared to empirically developed ranges associated with known failures to determine the failure mode (e.g., lead failure, gold-to-gold failure, ceramic pullout).

8 Claims, 7 Drawing Figures

METHODS FOR DETERMINING BOND FAILURE MODES USING STRESS WAVE EMISSION TECHNIQUES

TECHNICAL FIELD

This invention is directed to a real-time evaluation of bonds. In particular, the invention is directed to methods for determining failure modes of bonds during destructive testing.

BACKGROUND OF THE INVENTION

Manufacturers of microelectronic components often use thermocompression (TC) bonding to join external leads to film integrated circuits. TC bonds are known to be reliable provided the optimum parameters of time, temperature and pressure are used. The optimization of these parameters is obtained by analyzing the bond failure mode (e.g., lead failure, ceramic pullout) after destructive pull testing and adjusting the parameters accordingly. This process requires topographic examination, by conventional microscopy and/or scanning electron microscopy, of bonds which have been pulled to failure. Such detailed examination of the destroyed bond is subjective, time consuming, expensive and cannot be accomplished in real-time.

Stress Wave Emission (SWE) signals are a special class of sounds that have been used to detect ceramic microcracking as set forth in U.S. Pat. No. 3,924,456. SWE signals are transient elastic waves generated by the rapid release of strain energy from a localized source within a material. The SWE signal is characterized by a plurality of pulses having a low amplitude, short duration and a fast rise time.

U.S. Pat. No. 4,090,400 describes the non-destructive testing of a thermocompressively bonded beam lead device to determine the quality thereof by directing a short burst of air at the device and monitoring the bonds for SWE signals. The detected SWE signals are processed to determine the quality of the bond. Such a technique is most effective to measure bond quality, but if a bond failure occurs, there is no way to characterize the type of failure mode.

Accordingly, there exists a need for a real-time technique for determining the failure modes of bonds during destructive testing.

SUMMARY OF THE INVENTION

The instant invention overcomes the foregoing problem with a method for determining the failure mode of a bonded article during destructive testing. The method comprises the steps of monitoring the stress wave emissions emanating from the bonded article during the destructive test, developing a signal that is proportional to the number of excursions of the stress wave emissions above a predetermined threshold, and comparing the developed signal to empirically determined ranges of signals to determine the bond failure mode.

Advantageously, such a technique eliminates the detailed visual analysis of the bond area after destruction to determine the failure mode.

DETAILED DESCRIPTION

The instant invention will be described in relation to a real-time determination of failure modes of thermocompressive bonded gold plated leads to gold plated land areas on a ceramic substrate as the leads are pulled to destruction. However, it will be understood that such description is exemplary only and is for the purpose of exposition and not for limitation. It will be readily appreciated that the disclosed methods are applicable to other bonding techniques such as soldering, welding, brazing, etc. Additionally, the substrate may be one of many types of brittle substrate materials, such as aluminum oxide, beryllium oxide, silicon oxide, etc.

Figure 1:
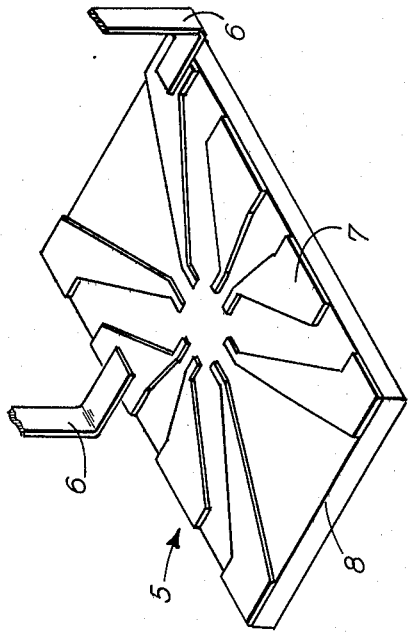
FIG. 1 is an isometric view of a hybrid integrated circuit having leads bonded thereto.

In the fabrication of a hybrid integrated circuit 5, as depicted in FIG. 1, it is common to thermocompressively bond gold plated leads 6—6 to gold coated land areas 7—7 on a ceramic substrate 8. To form the bond, a lead 6 is placed in contact with a land 7 and a thermocompression bonding tool head (not shown) is brought into contact with the lead for a time, pressure and at a temperature sufficient to bond the lead 6 to the land area 7. In order to determine whether the bonds are acceptable, a sample number of the bonded leads 6—6 are pulled to destruction and the force required is recorded. Additionally, each land area 7 (i.e., the bond site), as well as each lead 6, is visually examined by an operator to determine the failure mode, which may be ceramic pullout, fracture of the lead, separation at the gold-to-gold interface or the like. Once the failure mode has been determined, the bonding parameters (i.e., time, temperature, pressure) may be adjusted to provide a stronger and a more reliable bond. As hereinbefore indicated, such a subjective examination after each destructive test is time consuming, expensive and of questionable reliability. The instant invention overcomes such problems.

Figure 2:
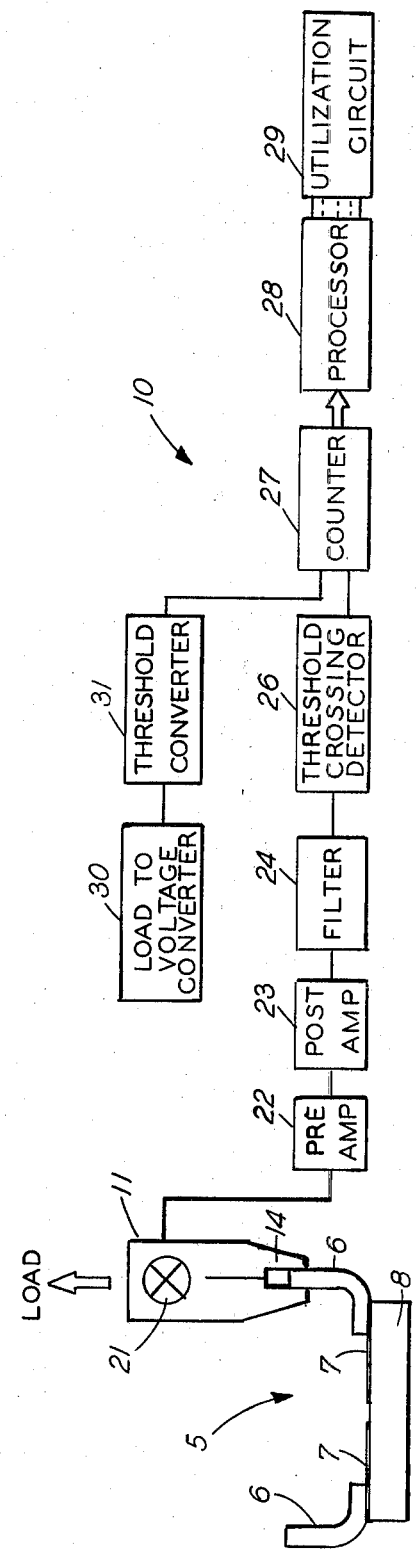
FIG. 2 is a block diagram of the instant method for determining failure modes using SWE techniques.

An exemplary embodiment of apparatus used to implement the instant invention is depicted in FIG. 2 and is generally referred to by the numeral 10. The apparatus 10 is comprised of a pulling mechanism 11 having a bifurcated end portion 14 to which a sensor 21 is fixedly mounted with an epoxy adhesive. The sensor 21 is a one megahertz piezoelectric type using a lead-zirconate-lead titanate K-350 crystal operating in the thickness vibrational mode. The sensor 21 was purchased from Keramos, Inc. located in Lizton, Indiana. The output of the sensor 21 is connected to the serial combination of a pre-amplifier 22, a postamplifier 23, a filter 24, a threshold crossing detector 26 and a counter 27. The output of the counter 27 is connected to the input of a processor 28 which, in turn, has an output connected to a utilization circuit 29. A load-to-voltage converter 30 is connected to a threshold detector 31 having an output terminated at an input of the counter 27.

In operation, the hybrid integrated circuit 5 (see FIG. 2) having a plurality of leads 6—6 (only two shown) thermocompressively bonded thereon is fixedly mounted in a workholder (not shown). The pulling mechanism 11 is positioned proximate the hybrid circuit 5 and the bifurcated end portion 14 clamped about one of the leads 6. A load is exerted in an upward direction by the mechanism 11 and the lead 6 is pulled until failure occurs. Most failures are due to breakage of the ductile lead 6, separation at the interface of the gold plated land and the gold plated lead, or ceramic pullout where the bond remains substantially intact but brittle ceramic material thereunder pulls off.

As the destructive pulling load is being applied, SWE signals emanating from the lead 6 or the land area 7 (i.e., the bond site) are transmitted through the pulling mechanism 11 to the sensor 21 and the detected signals are forwarded to the preamplifier 22 which is of a low noise type with a gain of 100 and passband of 600 KHz to 1.2 MHz. The signals are further amplified by the postamplifier 23 which also has a gain of 100 prior to passing through the filter 24 which is a third order, high pass passive type which filters out unwanted lower frequency noise (i.e., below 500 KHz).

Figure 3:
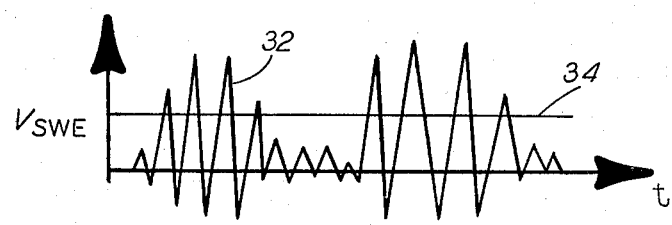
FIG. 3 is a plot of SWE signal voltage versus time.
Figure 4:
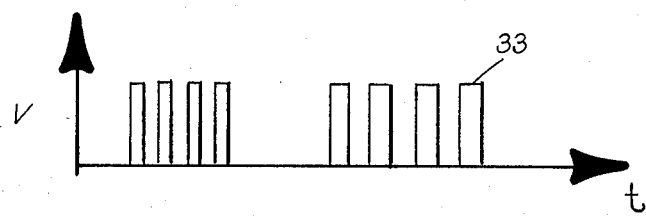
FIG. 4 depicts pulses which are generated for each SWE signal excursion above a threshold shown in FIG. 2.
Figure 5:
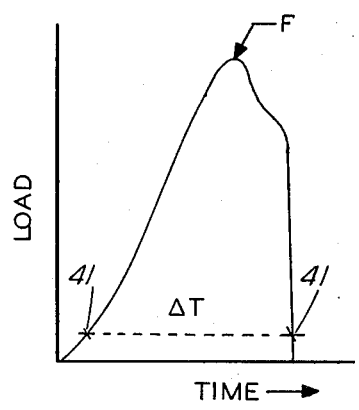
FIG. 5 is a plot of the pull force exerted on a bonded lead versus time.

The amplified and filtered SWE signals, indicated by numeral 32 in FIG. 3, are forwarded to the threshold crossing detector 26 where a pulse 33 (see FIG. 4) is generated for each excursion of the signal above a preset threshold value 34 shown in FIG. 3. The pulses 33—33 are forwarded to the counter 27 which sums the number of pulses occurring in time period $\Delta T$ (see FIG. 5) and forwards the sum to the processor 28. The time period $\Delta T$ is determined by converting the load or force F exerted on the lead 6 into a voltage by the converter 30. That voltage is passed to the threshold converter 31 which generates an output pulse to enable the counter 27 when the load F exceeds a preset value 41 and removes the enable pulse when the load F falls below that value.

The processor 28, which may be a programmed microprocessor or comprised of one or more comparators, will compare the count to one or more empirically developed ranges of counts, each range being indicative of a different failure mode. The microprocessor 28 will pass information indicative of the failure mode to the utilization circuit 29 which may be a visual display and/or a recorder. The count ranges were developed by initially using the visual and optical techniques hereinbefore discussed. However, once the ranges have been established for a particular apparatus 10 using a known threshold 34, it is no longer necessary to rely on those techniques.

Figure 6:
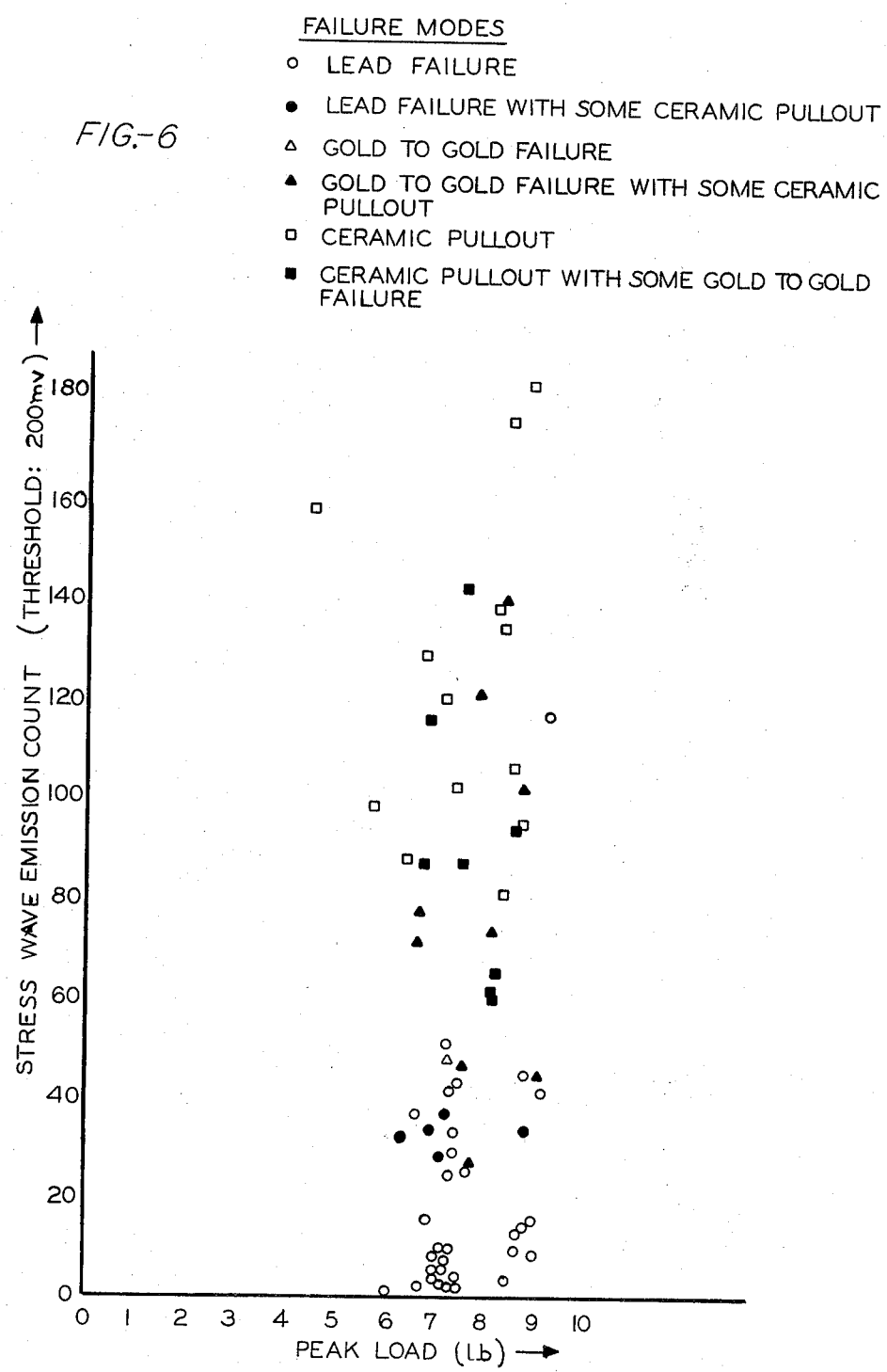
FIG. 6 is a plot of SWE pulse count for failures versus peak load using a threshold of 200 mv.
Figure 7:
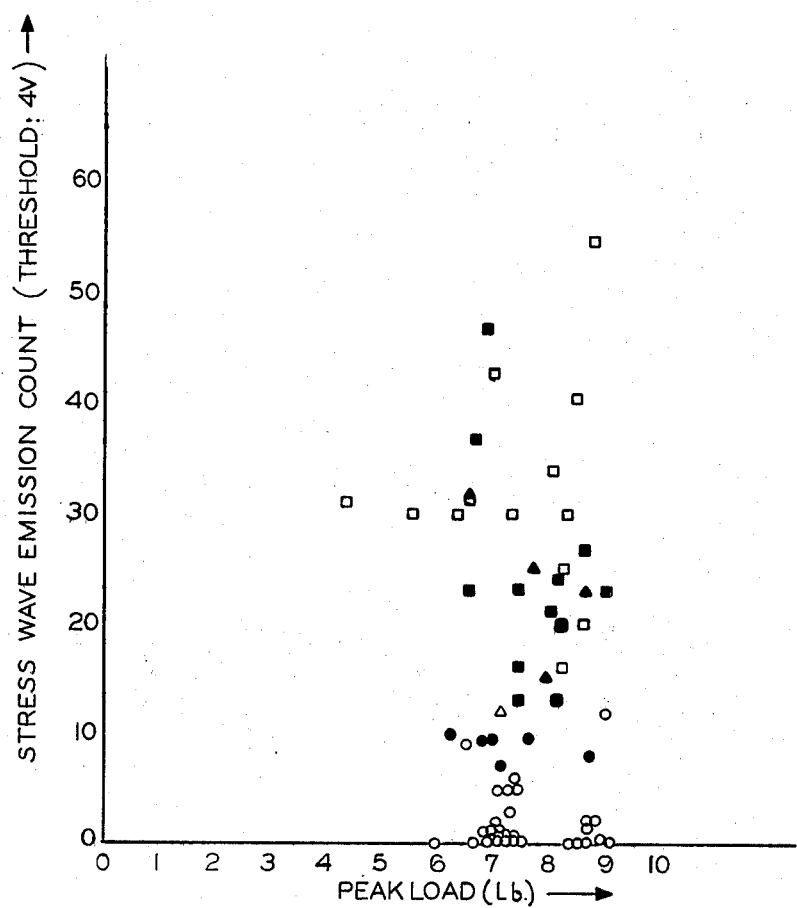
FIG. 7 is a plot of SWE count for failures versus peak load using a threshold of 4 v.

The SWE count for a single destructive test of a lead 6 has been found to depend on the type of failure mode. The plots in FIGS. 6 and 7 depict various failure modes plotted against the peak load and the SWE count associated with the failure. The voltage of threshold 34 is 200 mv for the data accumulated in FIG. 6, while a higher threshold of 4 volts was used for the FIG. 7 data. It can be seen that the SWE count is highest for ceramic pullout while the lower SWE count is related to lead failure, a middle range of counts is associated with failure at the gold-to-gold interface and mixed failure modes. It can also be seen that the peak load information bears no relationship to any specific failure mode and that the accuracy of determining the failure modes was increased as the threshold was increased from 200 mv to 4 volts.

Specifically, when using the higher threshold of 4 volts shown in FIG. 7, it was found that the SWE count is less than 6 for the lead failure mode and higher than 28 for ceramic pullout. The gold-to-gold failure modes and mixed modes (gold-to-gold with some ceramic pullout and lead failure with some ceramic pullout, etc.) fall within the range from 6 to 28 counts.

There is some scatter in the data of FIG. 7; for example, two data points which were determined to be a lead failure show an SWE count greater than 6. This scatter is probably due to the inadequacy of classifying failure modes using the present visual inspection technique such as a conventional optical microscope. Use of an auger electron spectroscope and chemical analysis to empirically establish the SWE count ranges should improve the accuracy of data and further enhance the accuracy of the instant technique. FIG. 6 shows the same trends of failure modes but exhibits more scatter than the data of FIG. 7. This is due to the lower threshold voltage (200 mv) being less effective in discriminating higher amplitude signals generated by ceramic pullout.

Advantageously, the instant method provides a technique for determining the failure mode of a bonded lead as it is pulled to destruction during a pull test. A plurality of failure modes may be automatically distinguished, eliminating the subjective and often inaccurate prior art techniques.

What is claimed is:

1. A method for determining the failure mode of a bonded article during destructive testing, comprising the steps of:
    monitoring the stress wave emissions emanating from the bonded article during the destructive test;
    developing a signal that is proportional to the number of excursions of the stress wave emissions above a predetermined threshold; and
    comparing the developed signal to empirically determined ranges of signals associated with known failure modes to determine the bond failure mode.

2. A method for determining the failure mode of a bonded article during destructive testing, comprising the steps of:
    monitoring the stress wave emission signals emanating from the bonded article during the destructive test;
    counting the number of stress wave emission pulses above a predetermined threshold; and
    comparing the pulse count to ranges of counts associated with specific failure modes to determine the failure mode of the bonded lead.

3. A method for determining the failure mode of a lead bonded to a substrate as a destructive pulling force is applied thereto, comprising the steps of:
    (a) detecting stress wave emission signals generated in the vicinity of the bond during the application of the destructive force;
    (b) amplifying and monitoring the detected signals;
    (c) counting the number of excursions of the stress wave emission signals above a predetermined threshold; and
    (d) comparing the excursion count to ranges of counts that are associated with specific failure modes to determine the failure mode of the bonded lead.

4. The method as set forth in claims 1, 2 or 3 which comprises the further step of:
    converting the results determined in the comparing step to a visual indication of the failure mode.

5. The method as set forth in claims 1 or 2 wherein the article is thermocompressively bonded.

6. The method as set forth in claims 1 or 2 wherein the article is solder bonded.

7. The method as set forth in claim 3 wherein the lead is thermocompressively bonded to the substrate.

8. The method as set forth in claim 3 wherein the lead is solder bonded to the substrate.

* * * * *